(12) United States Patent
Kim (10) Patent No.: US 12,239,564 B2
(45) Date of Patent: Mar. 4, 2025

(54) LEG PROTECTOR

(71) Applicant: Choonghwan Kim, Seoul (KR)

(72) Inventor: Choonghwan Kim, Seoul (KR)

( * ) Notice: Subject to any disclaimer, the term of this patent is extended or adjusted under 35 U.S.C. 154(b) by 325 days.

(21) Appl. No.: 17/851,388

(22) Filed: Jun. 28, 2022

(65) Prior Publication Data

US 2023/0062522 A1     Mar. 2, 2023

(30) Foreign Application Priority Data

Aug. 25, 2021   (KR) ........................ 10-2021-0112219

(51) Int. Cl.
     *A61F 5/058*      (2006.01)
     *A61F 13/04*      (2006.01)

(52) U.S. Cl.
     CPC .......... *A61F 5/0585* (2013.01); *A61F 13/043* (2013.01)

(58) Field of Classification Search
     CPC .... A61F 5/0585; A61F 13/043; A61F 5/0111; A61F 5/0127; A61F 5/0116; A43B 3/244; A43B 13/36; A43B 3/0047; A43B 7/19; A43B 7/20; A43B 13/16; A43B 13/28; A43B 3/02; A43B 5/16; A43B 5/1691; A43B 5/0403; A43B 5/0405; A43B 5/0409; A43B 5/0417; A43B 5/0421; A43B 5/0423; A43B 5/0435; A43B 5/0437; A43B 5/0439; A43B 5/045; A43B 5/0452; A43B 5/0464

See application file for complete search history.

(56) References Cited

U.S. PATENT DOCUMENTS 5,954,075 A   *   9/1999   Gilmour ............... A61F 5/0127
                                                            135/65
2004/0194351 A1 *   10/2004   Gallegos ................ A43C 15/02
                                                                36/44

FOREIGN PATENT DOCUMENTS

| JP | 3126681 U | 11/2006 | |
|---|---|---|---|
| JP | 2019048145 B2 | 3/2019 | |
| KR | 101520409 B1 | 5/2015 | |
| KR | 1020170107884 A | 9/2017 | |
| KR | 102102700 A | 4/2020 | |
| KR | 102232398 B1 * | 5/2020 | ............. A61H 39/04 |

* cited by examiner

*Primary Examiner* — Ophelia A Hawthorne
(74) *Attorney, Agent, or Firm* — Dinsmore & Shohl LLP; Yongsok Choi, Esq.

(57) ABSTRACT

The present disclosure relates to a leg protector. The leg protector according to an example embodiment of the present disclosure includes: a protection part formed to surround at least a portion of a user's leg; a bottom plate part formed integrally with the protection part and configured to support a user's foot; and a midsole provided below the bottom plate part, wherein at least one hole is formed in the bottom plate part, a protrusion portion is formed in the midsole at a position corresponding to the at least one hole, and the protrusion portion of the midsole is configured to be inserted into the at least one hole of the bottom plate part so that the bottom plate part and the midsole are coupled to each other.

7 Claims, 6 Drawing Sheets

LEG PROTECTOR

CROSS-REFERENCE TO RELATED APPLICATION

This application claims priority to Korean Patent Application No. 10-2021-0112219 filed on Aug. 25, 2021, the entire contents of which are herein incorporated by reference.

TECHNICAL FIELD

The present disclosure relates to a leg protector, and more particularly, to a leg protector having a structure which can improve user convenience.

BACKGROUND

When a person suffers an injury such as a sprain or fracture bone in his/her foot or leg, the person needs to immobilize his/her foot or leg to minimize movement in addition to a physical treatment. To do this, a method of immobilizing the foot or leg with a splint or cast has been widely used. However, in the case of using the splint or cast, several members are needed to immobilize the foot or leg. This restricts the movement too much, which makes walking and other physical activities be difficult.

To solve such matters, there is known a leg protector which is formed in the form of a ski boot to protect and support the leg while facilitating movement of the lag. This leg protector is made of a metal or a hard synthetic resin so as to be able to serve as a splint, and a bottom plate part which is in contact with the foot is also made of a hard material. The leg protector is convenient for use than the splint or cast. However, in the structure of the existing leg protector, shock may be applied to the foot at the time of walking. This may cause inconvenience to the user. In some cases, it may make the injury worse or cause another injury.

Accordingly, there is still a need for a leg protector having a structure that is capable of distributing the load acting on the foot at the time of walking to alleviate the shock while immobilizing and protecting the leg in a stable manner, thereby improving user convenience.

SUMMARY

One object of the present disclosure is to solve the aforementioned problems in the related art.

Another object of the present disclosure it to provide a leg protector which is capable of absorbing shock applied to a user's foot at the time of walking and distributing the load acting on the user's foot, thereby improving user convenience and safety.

According to one aspect of the present disclosure, there is provided a leg protector includes: a protection part formed to surround at least a portion of a user's leg; a bottom plate part formed integrally with the protection part and configured to receive a user's foot; and a midsole provided below the bottom plate part. At least one hole is formed in the bottom plate part, a protrusion portion is formed in the midsole at a position corresponding to the at least one hole, and the protrusion portion of the midsole is inserted into the at least one hole of the bottom plate part so that the bottom plate part and the midsole are coupled to each other.

According to one embodiment of the present disclosure, the at least one hole formed in the bottom plate part may be formed at a position corresponding to a heel of the user at a time of wearing the leg protector.

According to one embodiment of the present disclosure, the at least one hole formed in the bottom plate part may be formed to have a size corresponding to an area of the heel of the user.

According to one embodiment of the present disclosure, a number of the at least one hole formed in the bottom plate part may be one.

According to one embodiment of the present disclosure, the least one hole formed in the bottom plate part may include a plurality of holes, and the plurality of holes may be disposed adjacent to each other with at least one support provided between the plurality of holes.

According to one embodiment of the present disclosure, the protrusion portion of the midsole may be made of a material softer than a material of the bottom plate part.

According to one embodiment of the present disclosure, when the protrusion portion of the midsole is inserted into the at least one hole of the bottom plate part, at least a portion of the protrusion portion may protrude from an upper surface of the bottom plate part.

According to one embodiment of the present disclosure, the leg protector may further include an outsole configured to be detachably coupled to a lower portion of the midsole.

According to one embodiment of the present disclosure, at least one lateral protrusion may be formed on a side of the midsole, the outsole may include at least one insertion groove formed at a position corresponding to the at least one lateral protrusion, and the at least one lateral protrusion may be inserted into the at least one insertion groove so that the midsole and the outsole are coupled to each other.

According to another aspect of the present disclosure, there is provided a footwear which include: a protection part formed to surround at least a portion of a user's ankle; an insole coupled to the protection part and configured to receive a user's foot; and a midsole provided below the insole. At least one hole is formed in the insole, at least one protrusion portion is formed in the midsole at a position corresponding to the at least one hole, the at least one protrusion portion of the midsole is inserted into the at least one hole of the insole so that the insole and the midsole are coupled to each other, and the midsole is made of a material softer than a material of the insole.

According to the present disclosure, by inserting a protrusion portion formed in a midsole into a hole formed in a bottom plate part so as to couple the midsole to the bottom plate part, it is possible to absorb shock applied to a user's foot and distribute load acting on the user's foot, thus improving user convenience and safety.

DETAILED DESCRIPTION

Hereinafter, preferable embodiments of the present disclosure will be described in detail with reference to the accompanying drawings at such an extent that they may be practiced by those ordinary skilled in the art.

In order to clearly describe the present disclosure, detailed descriptions of parts irrelevant to the present disclosure will be omitted, and the same reference numerals will be given to the same elements throughout the specification. Further, a size, a thickness, a position and the like of each element illustrated in the drawings are arbitrarily illustrated for the sake of convenience in description, and hence the present disclosure is not necessarily limited to those illustrated. That is, it is to be understood that specific shapes, structures, and characteristics described herein may be modified from an example embodiment to another embodiment without departing from the spirit and scope of the present disclosure. Positions or arrangements of individual elements may also be modified without departing from the spirit and scope of the present disclosure.

Therefore, the following detailed description is not to be taken in a limiting sense, and the scope of the present disclosure is to be taken as encompassing the scope of the appended claims and all equivalents thereof.

Figure 1:
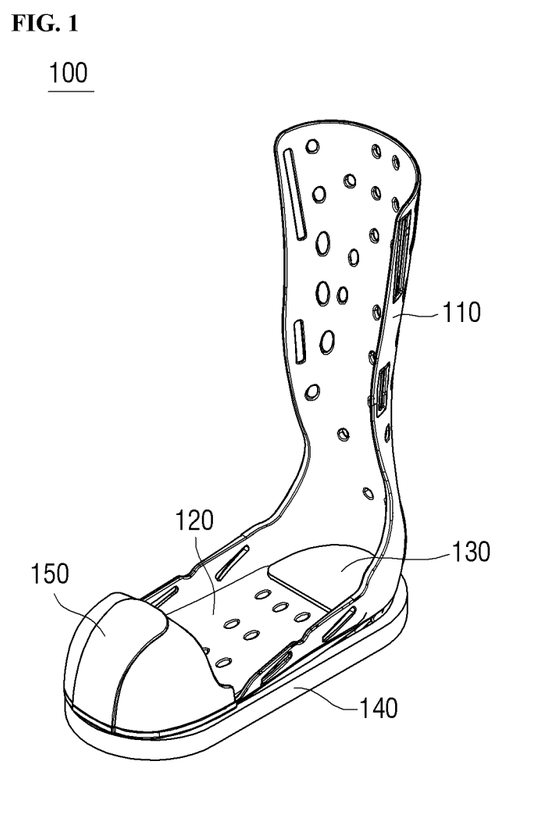
FIG. 1 is a perspective view of a leg protector according to one embodiment of the present disclosure.
Figure 2:
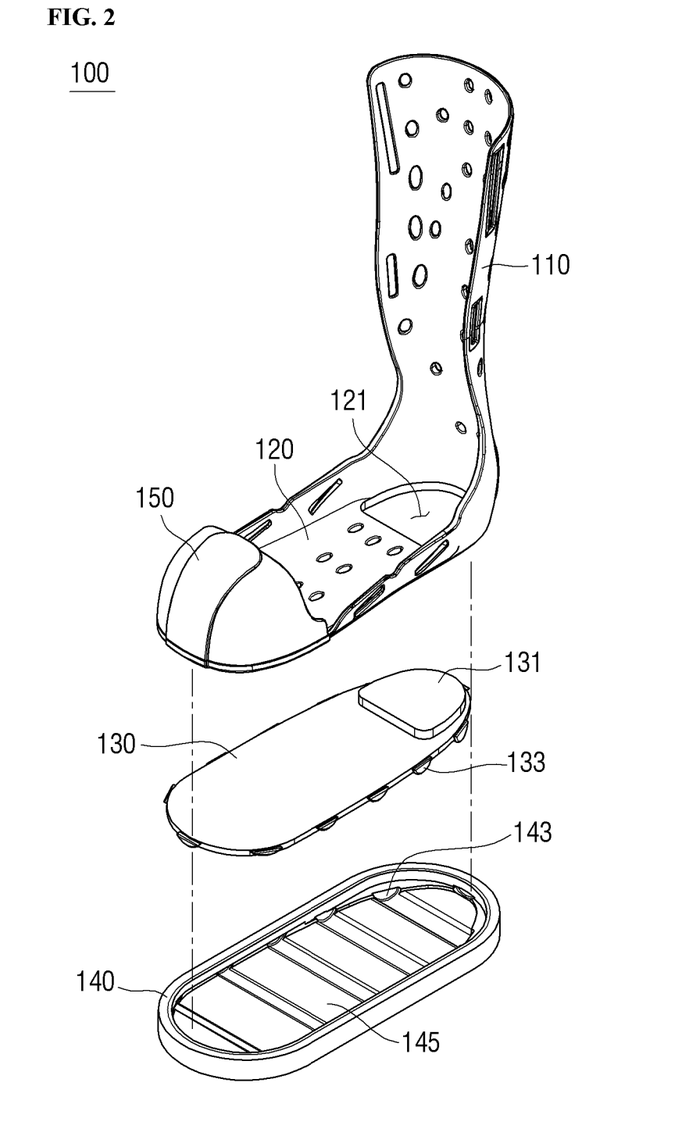
FIG. 2 is an exploded view of the leg protector according to one embodiment of the present disclosure.

FIG. 1 is a perspective view of a leg protector according to one embodiment of the present disclosure, and FIG. 2 is an exploded view of the leg protector according to one embodiment of the present disclosure.

Referring to FIGS. 1 and 2, a leg protector 100 according to one embodiment of the present disclosure may include a protection part 110, a bottom plate part 120, a midsole 130, an outsole 140, and a toe cap 150.

The protection part 110 of the leg protector 100 according to one embodiment of the present disclosure performs a function of fixing and protecting user's leg. To do this, the protection part 110 has a shape that surrounds at least a portion of the leg, that is, at least a portion of the side surface portion and the rear surface portion of the leg. Specifically, the protection part 110 may be configured to include a rear surface portion that supports the rear surface of the leg, and left and right side surface portions that support both sides of the leg. The left and right side surface portions may be formed in a bilaterally symmetric relationship.

A plurality of slits into each of which a connection member such as Velcro may be inserted, may be formed in each of the left and right side surface portions of the protection part 110 in a bilaterally symmetric relationship. Further, a plurality of ventilation holes may be formed in the protection part 110 for sweat release and ventilation. This reduces the overall weight of the leg protector 100.

The bottom plate part 120 of the leg protector 100 according to one embodiment of the present disclosure performs a function of fixing and supporting the foot. The bottom plate part 120 may be formed in a plate shape in a bilaterally symmetric relationship to be applied to both the left and right foots. Further, the bottom plate part 120 may be made of a relatively hard material, for example, a metal or a hard synthetic resin, so as to be able to stably support the foot.

Preferably, the bottom plate part 120 may be formed integrally with the protection part 110 and may be formed of the same material as the protection part 110. However, the present disclosure is not limited thereto. The protection part 110 and the bottom plate part 120 may be configured to be separated from each other and bonded to each other by a known coupling part.

The midsole 130 of the leg protector 100 according to one embodiment of the present disclosure is disposed below the bottom plate part 120 to perform a function of absorbing shock when walking. The midsole 130 may be formed in a plate shape in a bilaterally symmetric relationship in conformity to a shape of the bottom plate part 120. According to one embodiment of the present disclosure, the midsole 130 may be made of a softer material than that of the bottom plate part 120 for shock absorption and load dispersion. For example, the midsole 130 may be made of ethylene-vinyl acetate (EVA), urethane, polyurethane (PU), foaming sponge, rubber, or the like.

Surfaces of the midsole 130 and the bottom plate part 120 which face each other, that is, an upper surface of the midsole 130 and a lower surface of the bottom plate part 120, may be firmly bonded to each other by an adhesive. Further, in one embodiment of the present disclosure, at least one hole may be formed in the bottom plate part 120 and at least one protrusion may be formed in the midsole 130. The bottom plate part 120 and the midsole 130 may be coupled to each other by allowing a portion of each of the at least one protrusion formed in the midsole 130 to be inserted into the at least one hole formed in the bottom plate part 120. A coupling structure of the bottom plate part 120 and the midsole 130 will be described in more detail.

Figure 3:
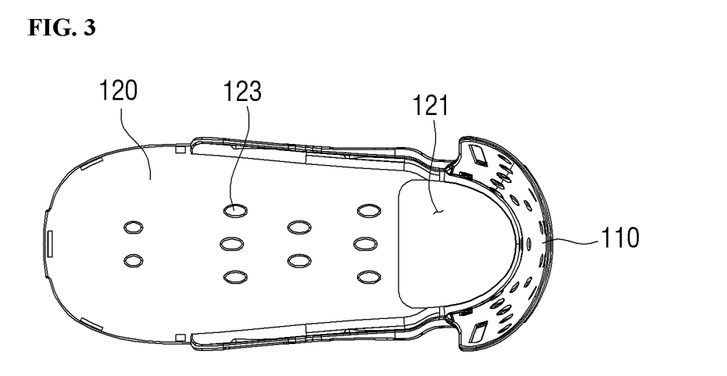
FIG. 3 illustratively shows the leg protector according to one embodiment of the present disclosure when viewed from the above.
Figure 4:
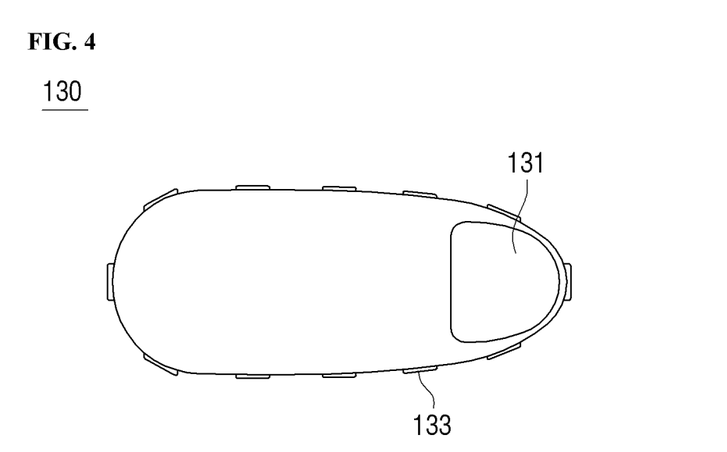
FIG. 4 illustratively shows a midsole of the leg protector according to one embodiment of the present disclosure when viewed from the above.

FIG. 3 illustratively shows the leg protector according to one embodiment of the present disclosure when viewed from the above, and FIG. 4 illustratively shows the midsole of the leg protector according to one embodiment of the present disclosure when viewed from the above.

Referring to FIG. 3, a hole 121 may be formed in the bottom plate part 120 of the leg protector 100 according to one embodiment of the present disclosure at a position adjacent to a portion connecting the protection part 110 and the bottom plate part 120, that is, a position corresponding to the heel of the user at the time of wearing the leg protector 100. The hole 121 formed in the bottom plate part 120 may be formed to have a size corresponding to or greater than the area of the heel of the user. The hole 121 may be formed in an approximately semicircular shape along a rear edge of the bottom plate part 120. When the size of the hole 121 is too large, the adhesive force between the lower surface of the bottom plate part 120 and the upper surface of the midsole 130 may be reduced. Thus, the size of the hole 121 may be determined in consideration of a user who will use the leg protector 100, the adhesive force between the midsole 130 and the bottom plate part 120, and the like.

In one embodiment, a large number of ventilation holes 123 may be dispersedly formed in the bottom plate part 120 in addition to the hole 121 described above. These ventilation holes 123 may perform a function of allowing sweat release and ventilation.

Referring to FIG. 4, the midsole 130 of the leg protector 100 according to one embodiment of the present disclosure may include a protrusion portion 131 formed at a position corresponding to the hole 121 formed in the bottom plate part 120. The protrusion portion 131 may be configured to be inserted into and coupled to the hole 121 formed in the bottom plate part 120 when the bottom plate part 120 is coupled to the midsole 130. The protrusion portion 131 of the midsole 130 may be formed in a shape corresponding to the hole 121 of the bottom plate part 120, for example, in a semicircular shape having a relatively large size. According to one embodiment, the protrusion portion 131 may be coupled to the hole 121 in a press-fitting manner. Alternatively, the protrusion portion 131 may be loosely fitted into the hole 121.

According to one embodiment of the present disclosure, at least a portion of the protrusion portion 131 of the midsole 130 may be configured to protrude from the upper surface of the bottom plate part 120 when the protrusion portion 131 is inserted into the hole 121 of the bottom plate part 120. For example, the protrusion portion 131 of the midsole 130 may be configured to protrude by a length of about 3 to 7 mm from the upper surface of the bottom plate part 120 when being coupled to the hole 121 of the bottom plate part 120.

In general, when the user walks while wearing the leg protector 100, the load may be concentrated on the sole of the foot of the user, specifically, the heel of the user, and thus shock may be applied to the heel. With the coupling structure of the bottom plate part 120 and the midsole 130 according to one embodiment of the present disclosure, a portion of the midsole 130 penetrates the bottom plate part 120 and comes into direct contact with the sole of the user's foot, for example, the heel, which makes it possible to distribute the load when the user walks and alleviate the shock.

Further, according to one embodiment of the present disclosure, the midsole 130 may be formed to have an area smaller than that of the bottom plate part 120 when viewed from the above. At least one lateral protrusion 133 may be formed on the side of the midsole 130. The lateral protrusion 133 of the midsole 130 is provided to be coupled to the outsole 140. A structure and function of the lateral protrusion 133 will be described later.

Referring back to FIG. 2, the outsole 140 of the leg protector 100 according to one embodiment of the present disclosure is configured to be detachably coupled to the midsole 130 so as to surround the midsole 130 below the midsole 130. Further, the outsole 140 may be made of a stretchable material, such as EVA, urethane, PU, forming sponge, rubber, or the like.

When the leg protector 100 is used outdoors, the leg protector 100 may be used while being coupled to the outsole 140, and when the leg protector 100 is used indoors, the leg protector 100 may be used in a state in which the outsole 140 is separated from the leg protector 100. With this configuration, it is possible to eliminate the need to put on or take off the entire leg protector 100 when moving indoors and outdoors, which improves the usability of the leg protector 100 while maintaining cleanliness thereof.

The outsole 140 may be formed larger in size than the midsole 130 to surround the midsole 130. In order to couple the outsole 140 to the midsole 130, the at least one lateral protrusion 133 may be formed on the side of the midsole 130 as described above, and an insertion groove 143 may be formed in the outsole 140 at a position corresponding to the lateral protrusion 133 of the midsole 130.

Figure 5:
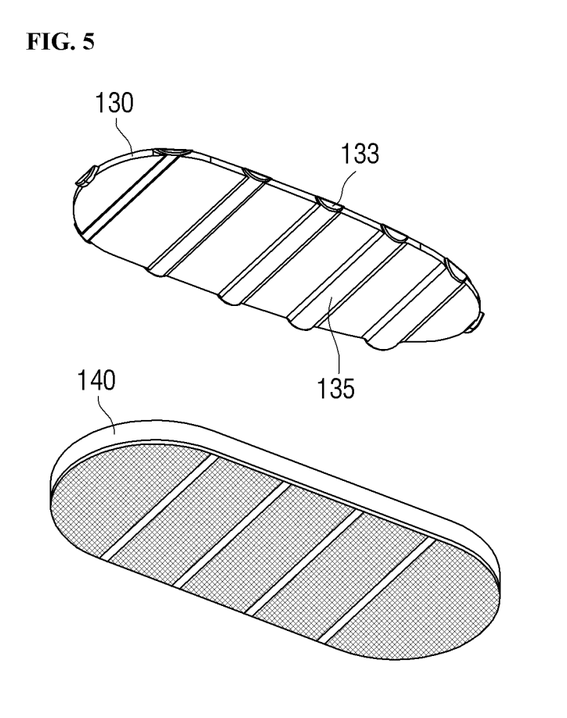
FIG. 5 illustratively shows a state in which the midsole and an outsole of the leg protector according to one embodiment of the present disclosure are disconnected from each other.

FIG. 5 illustratively shows a state in which the midsole and the outsole of the leg protector according to one embodiment of the present disclosure are disconnected from each other. As illustrated in FIG. 5, when the midsole 130 is coupled to the outsole 140, the lateral protrusion 133 of the midsole 130 may be inserted into the insertion groove 143 of the outsole 140 formed at the position corresponding to the lateral protrusion 133 while moving inward of the outsole 140 because both the midsole 130 and the outsole 140 are made of a stretchable material. The shape and number of lateral protrusions 133 and insertion grooves 143 are not limited to those illustrated in the figure, and may be changed in consideration of a coupling maintenance force, ease of detachment, and the like.

A first flexure 135 is formed on the lower surface of the midsole 130, and a second flexure 145 is formed on the upper surface of the outsole 140 to have a shape corresponding to the first flexure 135 of the midsole 130. Thus, when the midsole 130 and the outsole 140 are coupled to each other, the lateral protrusions 133 may be fitted into the respective insertion grooves 143, and simultaneously the first flexure 135 of the midsole 130 may be surely mounted on the second flexure 145 while sliding over the curved shape of the second flexure 145 of the outsole 140.

According to one embodiment of the present disclosure, the midsole 130 may be made of a material harder than that of the outsole 140. Thus, when the midsole 130 is coupled to the outsole 140, the outsole 140 may be expanded so that the midsole 130 is easily inserted into the outsole 140. When the outsole 140 is separated from the midsole 130, the outsole 140 may bend flexibly so that the outsole 140 is easily separated from the midsole 130. In a modified exemplary embodiment, the midsole 130 and the outsole 140 may be made of the same material.

As described above, the outsole may be coupled to or separated from the midsole in a simplified manner, for example, in a press-fitting manner of pressing the midsole against the outsole placed on the bottom from the above. Further, the leg protector 100 may be used both indoors and outdoors by coupling or separating the outsole to or from the midsole. This improves user convenience.

Further, protrusions or grooves may be formed on the lower surface of the outsole 140 to prevent slippage, or an anti-slip member may be coupled to the lower surface of the outsole 140 to prevent slippage on the lower surface of the outsole 140.

Referring back to FIG. 2, the toe cap 150 of the leg protector 100 according to one embodiment of the present disclosure is formed in a shape that surrounds the toes from the above to perform a function of protecting the toes from external impact. The toe cap 150 may be configured to be detachable to the top of the front surface of the bottom plate part 120. That is, the toe cap 150 may be removed from the leg protector 100 if necessary.

Although one hole 121 of the bottom plate part 120 and one protrusion portion 131 of the midsole 130 corresponding to the hole 121 have been described to be formed in the above-described embodiment, the number and shapes of holes and protrusion portions may be varied.

Figure 6:
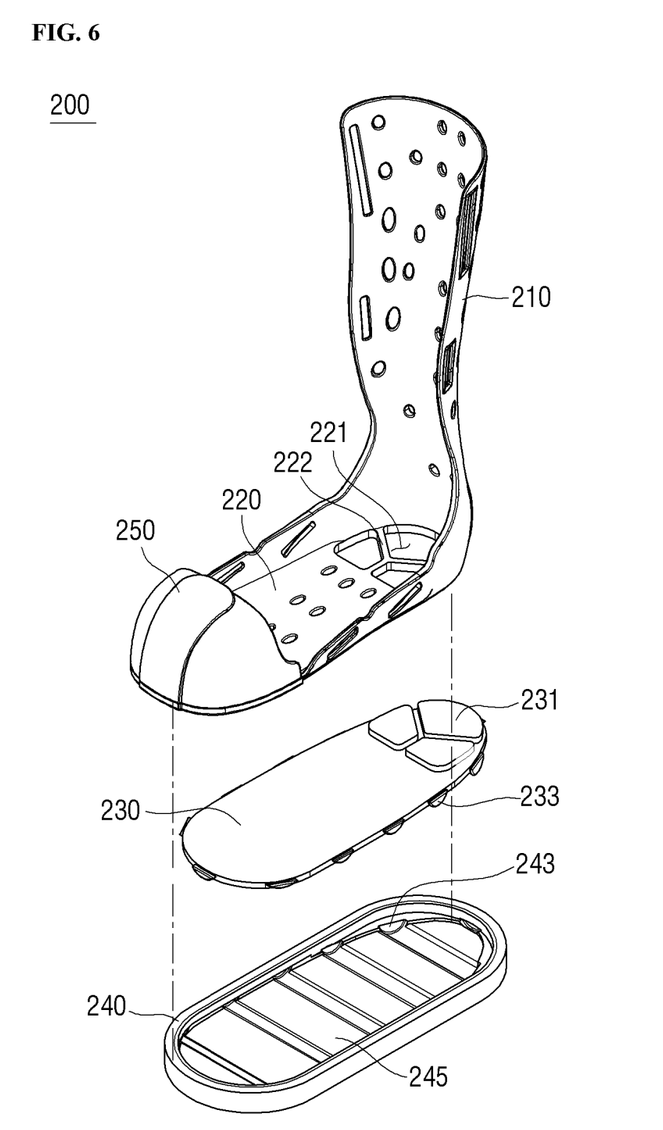
FIG. 6 is an exploded view of a leg protector according to another embodiment of the present disclosure.

FIG. 6 is an exploded view of a leg protector according to another embodiment of the present disclosure. Referring to FIG. 6, a leg protector 200 according to another embodiment of the present disclosure may be configured to include a protection part 210, a bottom plate part 220, a midsole 230, an outsole 240, and a toe cap 250, as in the above-described embodiment. Functions of elements of the leg protector 200 are substantially same as those of the above-described embodiment. However, the number of shapes of holes 221 formed in the bottom plate part 220 and protrusion portions 231 formed in the midsole 230 are different from those of the above-described embodiment. Hereinafter, such differences will be mainly described.

Figure 7:
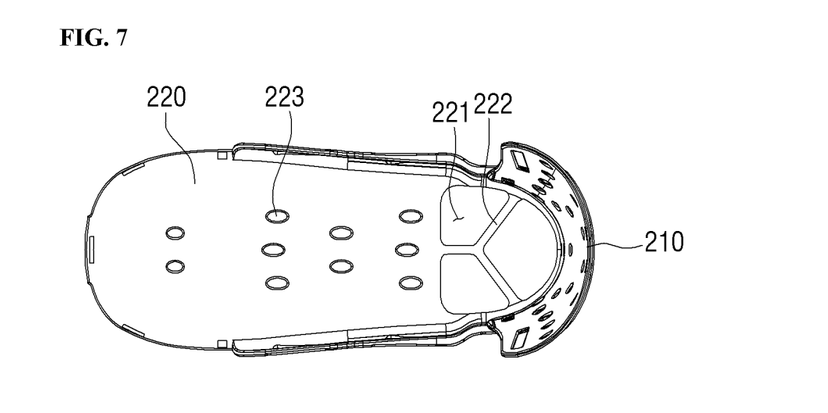
FIG. 7 illustratively shows the leg protector according to another embodiment of the present disclosure when viewed from the above.
Figure 8:
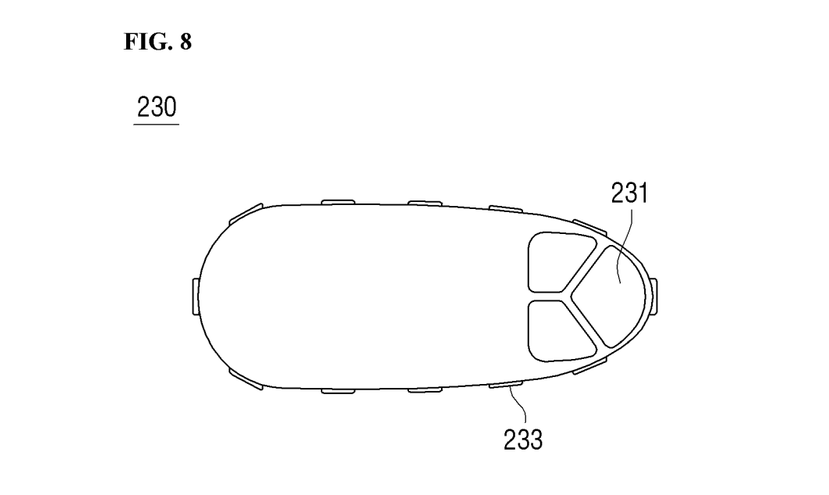
FIG. 8 illustratively shows a midsole of the leg protector according to another embodiment of the present disclosure when viewed from the above.

FIG. 7 illustratively shows the leg protector according to another embodiment of the present disclosure when viewed from the above, and FIG. 8 illustratively shows a midsole of the leg protector according to another embodiment of the present disclosure when viewed from the above.

Referring to FIG. 7, a hole 221 may be formed in the bottom plate part 220 of the leg protector 200 according to the present embodiment at a position corresponding to a region adjacent to a portion connecting the protection part 210 and the bottom plate part 220, that is, the heel of the user. According to the present embodiment, a plurality of holes 221 may be formed in the bottom plate part 220 with at least one support 222 provided therebetween. The plurality of holes 221 may be configured to have a semicircular shape that is generally similar to the shape of the heel. For example, three supports may be arranged in a radial shape, and three holes may be arranged adjacent to each other along a rear edge of the bottom plate part 220 with the respective support provided between the two adjacent holes. Thus, the holes 221 may be arranged in a semicircular shape as a whole. According to the present embodiment, the protrusion portions 231 of the midsole 230 may be inserted into and coupled to the respective holes 221 of the bottom plate part 220, and the bottom surface of the bottom plate part 220 including the lower surface of the support 222 may be bonded to and fixed to the midsole 230 by a known bonding method.

Referring to FIG. 8, the protrusion portion 231 may be formed in the midsole 230 of the leg protector 200 according to the present embodiment at positions corresponding to the holes 221 formed in the bottom plate part 220. The protrusion portions 231 of the midsole 230 may be formed in a shape corresponding to the respective holes 221 of the bottom plate part 220. As illustrated in FIG. 8, three protrusions may be arranged at a predetermined interval to form a semicircular shape as a whole.

With this configuration, in the present embodiment, by forming the support between the holes formed in the bottom plate part, it is possible to increase the coupling area of the midsole and the bottom plate part, and fix and couple the midsole to the bottom plate part in a more stable manner.

Although the present disclosure has been described above in terms of specific items such as detailed elements as well as the limited embodiments, they are merely provided to help more general understanding of the present disclosure, and the present disclosure is not limited to the above embodiments. Various modifications and changes could have been realized by those skilled in the art to which the present disclosure pertains from the above description.

For example, the configurations of the present disclosure described in the above embodiments may also be applied to a general footwear.

Specifically, the footwear according to the present disclosure may include a protection part formed to surround at least a portion of a user's ankle, an insole coupled to the protection part and configured to receive a user's foot when the user wears the footwear, and a midsole provided below the insole. The insole may include at least one hole formed at a position corresponding to a user's heel when the user wears the footwear. The midsole may include at least one protrusion portion formed at a position corresponding to the at least one hole formed in the insole. The at least one protrusion portion of the midsole is inserted into the at least one hole of the insole so that the insole and the midsole may be coupled to each other. Further, the midsole may be made of a material softer than that of the insole. This configuration provides the effects of dispersing the load acting on the user's foot when walking and absorbing shock to be applied to the user's foot.

Therefore, the spirit of the present disclosure need not to be limited to the above-described embodiments, and in addition to the appended claims to be described below, and all ranges equivalent to or changed from these claims need to be said to belong to the scope and spirit of the present disclosure.

What is claimed is:

1. A leg protector comprising:
a protection part formed to surround at least a portion of a user's leg;
a bottom plate part formed integrally with the protection part and configured to support a user's foot; and
a midsole provided below the bottom plate part,
wherein at least one hole is formed in the bottom plate part,
wherein a protrusion portion is formed in the midsole at a position corresponding to the at least one hole,
wherein the at least one hole is configured to be formed at a position corresponding to a heel of the user at the time of wearing the leg protector,
wherein the protrusion portion of the midsole is configured to be inserted into the at least one hole of the bottom plate part so that the bottom plate part and the midsole are coupled to each other, and at least a portion of the protrusion portion protrudes from an upper surface of the bottom plate part,
wherein the midsole is made of a material softer than a material of the bottom plate part, and
wherein an upper surface of the midsole and a lower surface of the bottom plate part is firmly bonded to each other by an adhesive.

2. The leg protector of claim 1, further comprising an outsole configured to be detachably coupled to a lower portion of the midsole.

3. The leg protector of claim 2, wherein at least one lateral protrusion is formed on a side of the midsole, and
wherein the outsole includes at least one insertion groove formed at a position corresponding to the at least one lateral protrusion, and the at least one lateral protrusion is configured to be inserted into the at least one insertion groove so that the midsole and the outsole are coupled to each other.

4. The leg protector of claim 1, wherein the at least one hole formed in the bottom plate part is configured to be formed to have a size corresponding to an area of the heel of the user.

5. The leg protector of claim 1, wherein a number of the at least one hole formed in the bottom plate part is one.

6. The leg protector of claim 1, wherein the least one hole formed in the bottom plate part includes a plurality of holes, and the plurality of holes are disposed adjacent to each other with at least one support provided therebetween.

7. A footwear comprising:
a protection part formed to surround at least a portion of a user's ankle;
an insole coupled to the protection part and configured to support a user's foot; and
a midsole provided below the insole,
wherein at least one hole is formed in the insole,
wherein at least one protrusion portion is formed in the midsole at a position corresponding to the at least one hole, wherein the at least one protrusion portion of the midsole is configured to be inserted into the at least one hole of the insole so that the insole and the midsole are coupled to each other, wherein the at least one hole is configured to be formed at a position corresponding to a heel of the user at the time of wearing the leg protector, wherein the midsole is made of a material softer than a material of the insole, and at least a portion of the protrusion portion protrudes from an upper surface of the bottom plate part, wherein the midsole is made of a material softer than a material of the bottom plate part, and wherein an upper surface of the midsole and a lower surface of the bottom plate part is firmly bonded to each other by an adhesive.

\* \* \* \* \*